(12) United States Patent
Sardo

(10) Patent No.: US 9,072,291 B2
(45) Date of Patent: Jul. 7, 2015

(54) METHOD FOR PRODUCING A GAS FLOW CONTAINING AN ESSENTIAL OIL VAPOUR, METHOD FOR TREATING A SITE WITH SUCH A GAS, AND RELATED DEVICE

(71) Applicant: XEDA INTERNATIONAL, Saint Andiol (FR)

(72) Inventor: Alberto Sardo, Chateaurenard (FR)

(73) Assignee: XEDA INTERNATIONAL, Saint Andiol (FR)

( * ) Notice: Subject to any disclaimer, the term of this patent is extended or adjusted under 35 U.S.C. 154(b) by 103 days.

(21) Appl. No.: 13/845,219

(22) Filed: Mar. 18, 2013

(65) Prior Publication Data

US 2013/0306158 A1 Nov. 21, 2013

(30) Foreign Application Priority Data

May 21, 2012 (FR) ...................................... 12 54587

(51) Int. Cl.
*B01F 3/04* (2006.01)
*A01N 3/00* (2006.01)
*A23L 3/3409* (2006.01)
*A23B 7/144* (2006.01)
(Continued)

(52) U.S. Cl.
CPC .............. *A01N 3/00* (2013.01); *B01F 3/04049* (2013.01); *A23L 3/3409* (2013.01); *A23L 3/34095* (2013.01); *A23B 7/144* (2013.01); *B05B 7/0458* (2013.01); *B05B 7/1626* (2013.01); *B05B 7/1686* (2013.01); *A01N 25/00* (2013.01)

(58) Field of Classification Search
CPC .... B01F 3/04; B01F 3/04007; B01F 3/04014; B01F 3/04021; B01F 3/022

USPC ................... 261/76, 78.2, 118, 142, DIG. 65, 261/DIG. 88, DIG. 89; 422/124
See application file for complete search history.

(56) References Cited

U.S. PATENT DOCUMENTS

| 3,783,097 A | 1/1974 | Justus |
| 6,548,025 B1 | 4/2003 | Rasouli et al. |

(Continued)

FOREIGN PATENT DOCUMENTS

| AU | 625491 B3 | 7/1992 |
| EP | 0719499 A1 | 7/1996 |

(Continued)

OTHER PUBLICATIONS

Tyagi et al., "Bactericidal action of lemon grass oil vapors and negative air ions", Innovative Food Science and Emerging Technologies, 2012, vol. 13, pp. 169-177, XP 55050521A.

(Continued)

*Primary Examiner* — Robert A Hopkins
(74) *Attorney, Agent, or Firm* — Young & Thompson

(57) ABSTRACT

A method producing a gas flow containing an essential oil vapor includes the following steps:
creation of a pressurized gas flow with a controlled flowrate and a given temperature; and
injection into the pressurized gas flow of a liquid composition including at least one liquid essential oil, at a dosed flow rate;
whereby the flow rate of the gas flow and that of the liquid composition are controlled such that the gas flow, following injection, has a partial essential oil vapor pressure of at least 20% below the saturation pressure of the essential oil vapor at the temperature of the gas flow.

16 Claims, 3 Drawing Sheets

Figure 1:
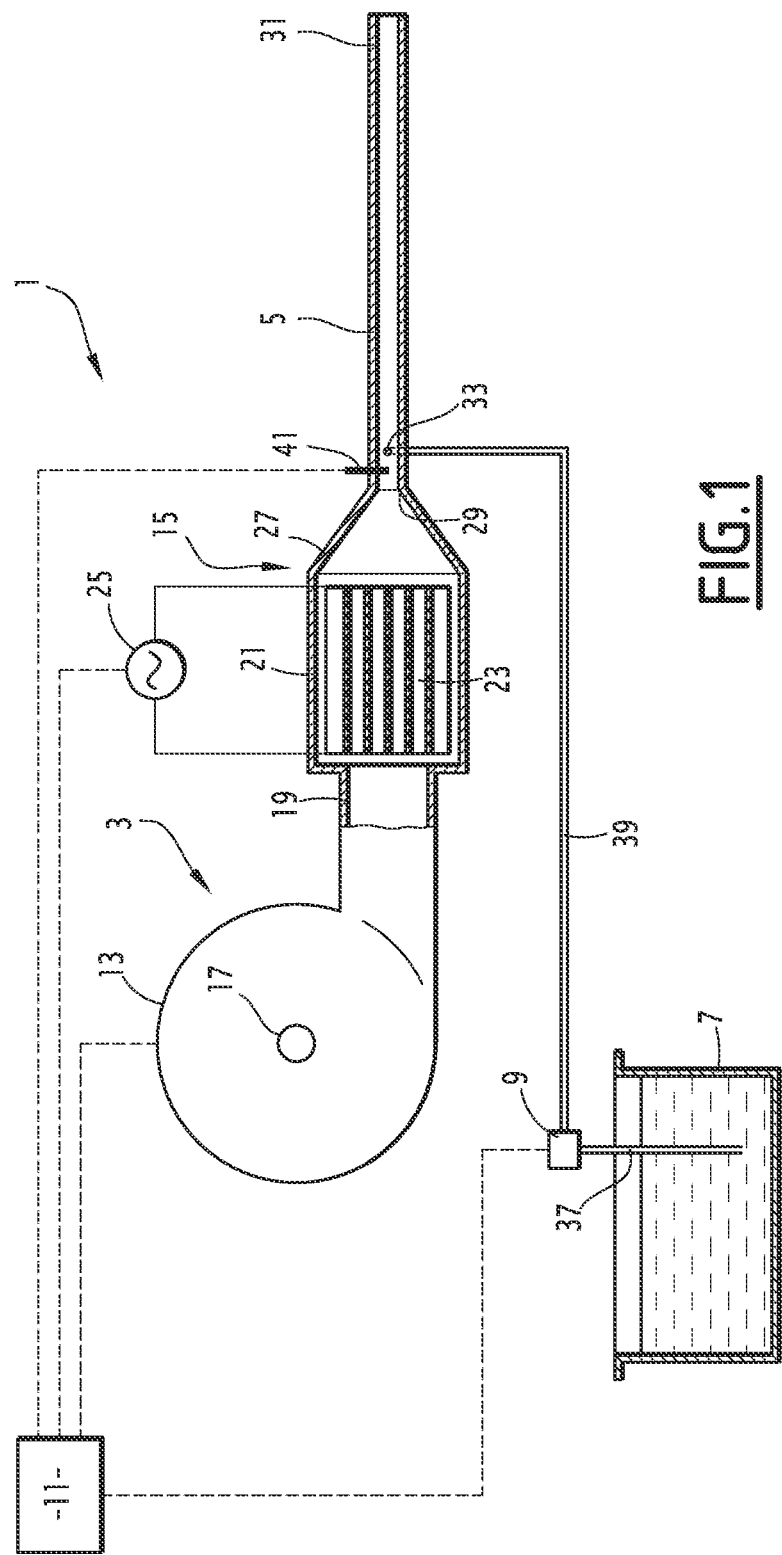
Figure 2:
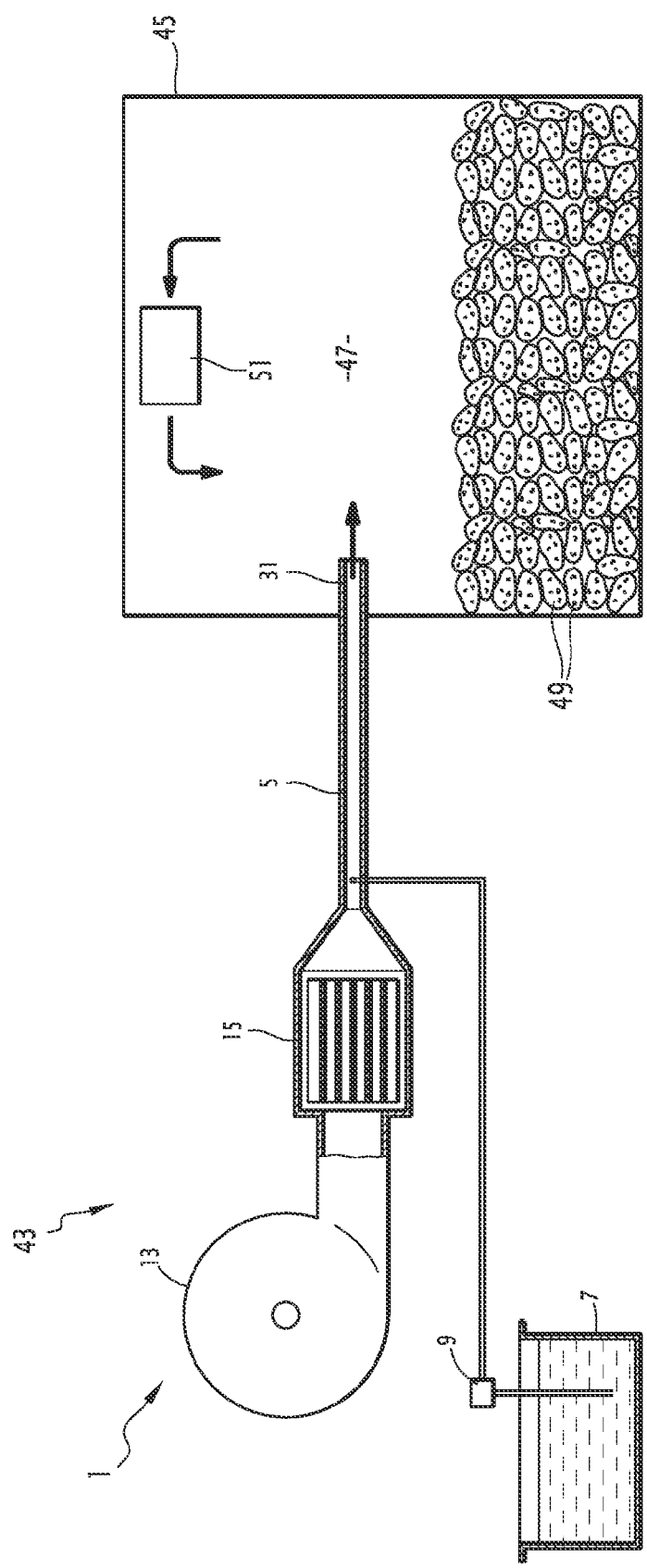

(51) Int. Cl.
   *B05B 7/04*   (2006.01)
   *B05B 7/16*   (2006.01)
   *A01N 25/00*   (2006.01)

(56) References Cited

U.S. PATENT DOCUMENTS 8,048,379 B2 * 11/2011 Sassoon .................... 422/124
2010/0123018 A1   5/2010 Sardo

FOREIGN PATENT DOCUMENTS

| EP | 2186573 | A1 | 5/2010 |
|---|---|---|---|
| FR | 2566681 | A1 | 1/1986 |
| FR | 2791910 | A1 | 10/2000 |
| FR | 2938458 | A1 | 5/2010 |
| FR | 2964887 | A1 | 9/2010 |
| WO | 2009144465 | A2 | 12/2009 |
| WO | 2012177969 | A2 | 12/2012 |

OTHER PUBLICATIONS

Gardner et al., "Henaxal, trans-2-Hexenal, and trans-2-Nonenal Inhibit Soybean, Glycine max, Seed Germination", J. Agric. Food Chem., 1990, vol. 38, pp. 1316-1320, XP55050707A.

French Search Report, dated Jan. 24, 2013, from corresponding FR application.

* cited by examiner

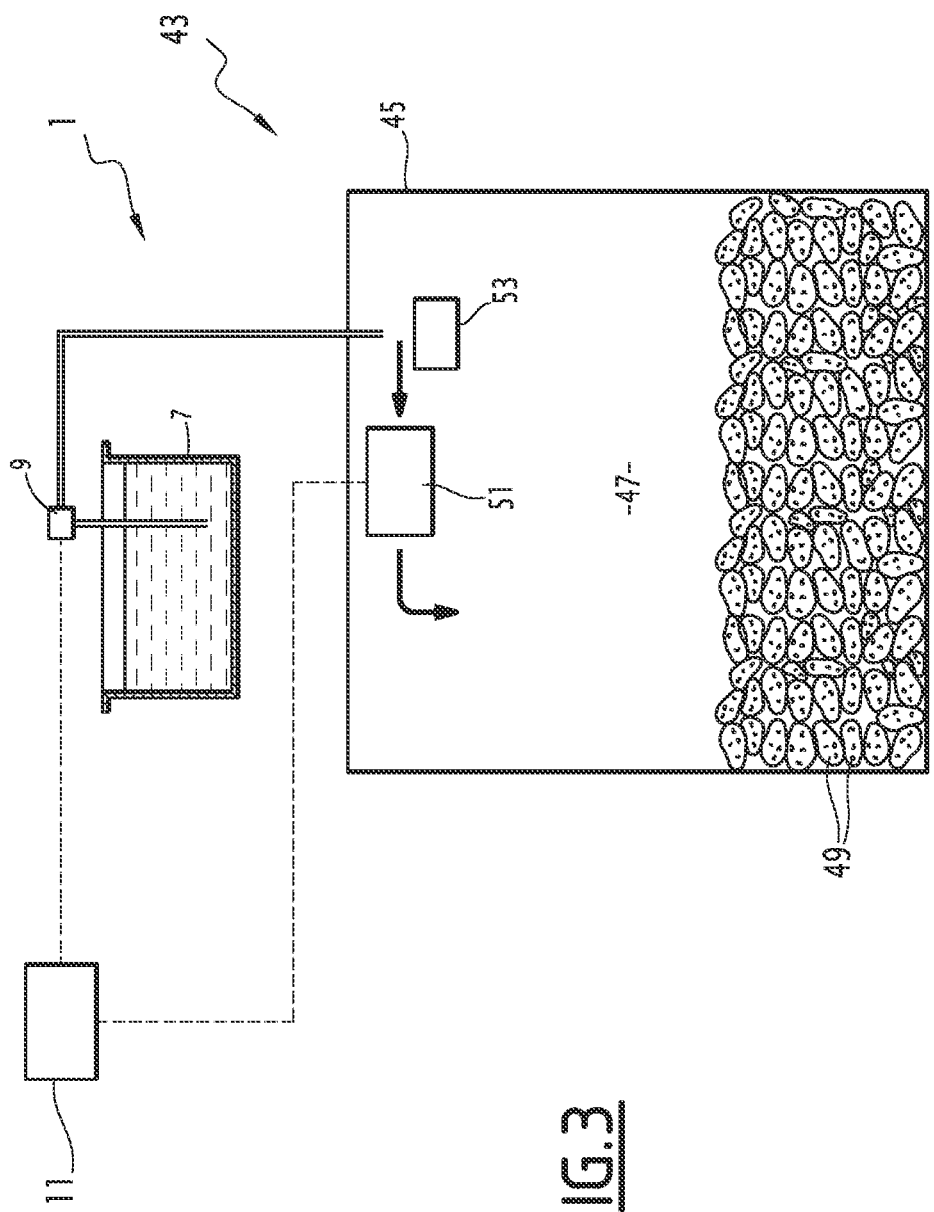

METHOD FOR PRODUCING A GAS FLOW CONTAINING AN ESSENTIAL OIL VAPOUR, METHOD FOR TREATING A SITE WITH SUCH A GAS, AND RELATED DEVICE

BACKGROUND OF THE INVENTION

1. Field of the Invention

This invention generally concerns sterilisation treatment by a vapour of essential oils intended for sites or plant matter. In the case of food products such as fruits and vegetables, the treatment seeks to extend their preservation. In the case of sites, the treatment seeks to sanitise them.

2. Description of the Related Art

WO 2009/144465 describes the possibility of using essential oil vapours, e.g., essential oils extracted from citrus fruits, to treat fresh foods and destroy or inhibit the growth of microorganisms contaminating those foods.

The industrial treatment of food products such as fruits and vegetables stored in storerooms, greenhouses, or silos requires the production of substantial amounts of vapour. Furthermore, the vapours must not condense and form droplets, which may settle on the food products. Such settled condensation may in fact be phytotoxic.

In this context, there is a need for a method that can produce substantial quantities of essential oil vapour without any risk of condensation.

SUMMARY OF THE INVENTION

To this end, the invention, according to a first aspect, concerns a method for producing a gas flow containing an essential oil vapour or a vapour of one or more terpenoid compounds contained in the essential oil, comprising the following steps:
- creation of a pressurised gas flow with a controlled flow-rate and a given temperature; and
- injection into the pressurised gas flow of a liquid composition comprising at least one liquid essential oil, at a dosed flow rate;
- whereby the flow rate of the gas flow and the flow rate of the liquid composition are controlled such that the gas flow, following injection, has a partial essential oil vapour pressure of at least 20% below the saturation pressure of the essential oil vapour at the temperature of the gas flow.

The injection of the liquid essential oil into the gas flow allows for extremely precise control of the essential oil vapour in the gas flow. It make it possible to work with a very high gas flow rate without the risk of essential oil droplets forming within the gas flow. To the contrary, the greater the gas flow rate, the faster and more efficient the dispersion and evaporation of the liquid essential oil.

In relation to a production method consisting of having a gas bubble in a bath including a liquid essential oil, it is possible to produce a much higher gas flow rate, and thus a much greater quantity of vapour. In fact, in the bubble method, the gas flow rate is limited. If the flow rate is too high, large liquid bubbles are driven with the gas, and these bubbles are not vaporised.

The liquid composition includes a single liquid essential oil. For example, the liquid includes a liquid essential oil chosen from the group of mint oil, clove oil, rose oil, thyme oil, oregano oil.

In one variant, the liquid comprises one of the constituents of these oils, chosen from L-carvone, eugenol, geraniol, thymol, or carvacrol.

In one variant, the liquid composition includes pyrethrum or synthetic pyrethrins, or any other volatile synthetic molecules with biocidal properties.

The liquid composition typically includes only a single liquid essential oil with no solvents or adjuvants. In one variant, the liquid includes an aqueous or organic solvent, in which the essential oil and/or one or more adjuvants is dissolved. The aqueous solvent is, e.g., water. The organic solvent is, e.g., a solvent of the type described in FR 2791910 or glycols, diglycols, and their respective esters The adjuvants are, e.g., substances suited to transport the active ingredient(s) or provide a diluting effect.

In one variant, the liquid composition includes a mixture of several liquid essential oils, e.g., several liquid essential oils from the list above.

The gas forming the gas flow is typically air. However, this gas, in one variant, is a neutral gas such as nitrogen, or any other gas or mixture of gases.

The saturation pressure of the essential oil vapour is the partial pressure of the essential oil vapour at which the essential oil begins to condense. It is specific to each essential oil, and varies based on the temperature. The partial pressure curve as a function of temperature is typically determined experimentally for each essential oil.

In the invention, the partial vapour pressure of the essential oil in the gas flow is kept below 20% at least at the saturation pressure of the essential oil vapour at the temperature of the gas flow, so as to avoid any condensation of the essential oil into droplets. A margin sufficient to minimise the risk of condensation is chosen. Such condensation may normally occur when the gas flow loaded with essential oil vapour is injected into the atmosphere of a site, e.g., a silo or a greenhouse for storing food products such as fruits and vegetables. This injection causes a reduction of the temperature of the gas flow, which tends to reduce the saturation pressure of the essential oil vapour. The margin is chosen to avoid condensation in this case. However, it should be noted that the injection also causes a dilution of the gas flow in the atmosphere and a reduction of the essential oil vapour concentration. This contributes to avoiding condensation.

Likewise, the storage areas for food products such as fruits and vegetables are generally equipped with fans to mix the internal atmosphere of the enclosure. The flow of gas loaded with essential oil vapour is preferably created or injected by the aspiration of the recirculation fans, which thus contribute to better distribution of the product in the atmosphere.

The margin of at least 20% with respect to the saturation pressure of the essential oil vapour, and the dilution, are considered sufficient to eliminate the risk of condensation related to increased discharge pressure of the fan.

Typically, the partial pressure of the essential vapour oil in the gas flow is kept below 20% at least at the saturation pressure of the essential oil vapour at the temperature of the gas flow, preferably below 30% or less, and more preferably below 40% or less.

Preferably, the gas flow is controlled at a value of 10-200 $Nm^3/h$, more preferably 20-100 $m^3/h$, and even more preferably 30-70 $m^3/h$. Such a flow allows for the vaporisation of a substantial amount of essential oil, sufficient to treat, e.g., several tonnes of plant matter.

Typically, the flow rate of the gas flow is constant for a given installation. It cannot be modified, and corresponds to the nominal flow rate of the organ used to produce the gas flow. In this case, the partial pressure of the essential oil vapour is controlled essentially by adjusting the amount of liquid injected compared to the amount of gas.

In one variant, the flow rate of the gas flow is adjustable, in particular by changing the scheme for the organ used to produce the gas flow. In this case, the partial pressure of the essential oil vapour may be controlled by modifying the amount of liquid injected and/or varying the flow rate of the gas flow.

Typically, the flow rate of the liquid composition is controlled so that the mass of essential oil injected into the gas flow is between 0.1 and 50 kg/h, preferably between 0.1 and 10 kg/h, and more preferably between 0.5 and 5 kg/h. In other words, the flow rate of the liquid composition is much lower than the flow rate of the gas flow, in volume and/or in mass. The dispersion and evaporation of the liquid composition are thus carried out very efficiently. As a result, it is not mandatory to work with a gas at high temperature to increase the saturation pressure of the essential oil vapour. It is easy to remain far from the saturation pressure, simply because the ratio between the quantity of essential oil injected and that of the gas is very low.

"Injection" here refers to the act of introducing, by a voluntary, affirmative action, a quantity of liquid composition into the gas flow. This differs, in particular, from methods such as bubbling, in which the transfer of the liquid composition in the gas flow is passive, and results solely from placing the gas flow into contact with the liquid composition.

Preferably, the liquid composition is injected using a dosing pump. Such a dosing organ allows for precise control of the quantity of liquid composition injected. It is well suited to the flow rate range intended for the liquid composition. In one variant, the liquid composition is injected by gravity, by the Venturi effect, or by any other suitable dosing organ.

The flow rate of the gas flow and that of the liquid composition are controlled, e.g., by a computer. The computer is programmed to control the organ creating the pressurised gas flow, the organ heating the gas flow, and the organ dosing the quantity of liquid injected. In one variant, one or more of these organs are manually controlled.

According to a first embodiment, the pressurised gas flow has a controlled temperature, said temperature being controlled such as the gas flow, following injection, has a partial essential oil vapour pressure at least 20% below the saturation pressure of the essential oil vapour at the controlled temperature.

According to this first embodiment, the pressurised gas flow is advantageously created by a blower. This is comfortable and economical. In one variant, the gas flow is created by a centrifugal fan.

According to this first embodiment, as well, the gas flow temperature is typically controlled by heating the gas flow via an electrical resistance arranged downstream of the blower. "Upstream" and "downstream" in this patent application are refer to the direction of circulation of the gas flow. In one variant, the gas flow is heated by a heat exchanger, or by any other suitable organ. The temperature is controlled in a closed loop by measuring the actual temperature of the gas flow and by adjusting the heat output depending on the measured temperature and a temperature setpoint. In one variant, the temperature is controlled in an open loop by fixing the heat output without measuring the actual temperature.

Advantageously, the temperature of the gas flow is controlled between 50° C. and 350° C., preferably 70° C. and 200° C. The temperature must be sufficient to promote the evaporation of the liquid essential oil. However, it is preferable not to go beyond 250° C. for the following reasons; Actively avoiding degradation at high temperature; avoiding any risk of fire; limiting the risk of condensation resulting from the temperature difference between the gas flow and the atmosphere into which the gas flow is injected.

The temperature of the gas flow is controlled, e.g., by a computer, advantageously by the same computer that controls the flow rate of the gas flow and that of the liquid composition.

According to a second embodiment, the liquid composition is deposited in a porous element arranged upstream of the pressurised gas flow production organ. In one variant, the porous element is arranged downstream of the gas flow production organ. The porous element is typically formed by a rubbery material such as an open-cell latex plate. In one variant, the porous element is a sponge or wadding. The porous element allows for storage of the liquid composition that is not injected into the gas flow.

According to a second aspect, the invention concerns a method for treating a site using a gas flow containing an essential oil vapour obtained according to the aforementioned method of production. In a first exemplary embodiment, the gas flow is provided to sterilise the atmosphere and surfaces of the site. The site is, e.g., a room in a hospital or school, or any other building.

In a second exemplary embodiment, the site is a confined area intended for the storage of plant matter. This area is typically a greenhouse, a refrigerated or non-refrigerated room, a building, or a storage silo. The area is confined, such that the air flow circulating from outside to inside the area is very low, and the air flow circulating from inside to outside of the area is very low, as well. The replacement rate of the air in the area is typically less than 20 volumes/day, taking the precaution that the replacement fans are not operating during the injection phases.

The method is used, e.g., when the area is empty. The gas flow containing the essential oil vapour allows for sterilisation of the atmosphere of the area, and avoidance of any contamination. It also allows for sanitising the internal surfaces of the area: Walls, woodwork . . . .

In one variant, the method is used when the area contains plant matter. This plant matter is, e.g., food products such as fruits or vegetables, e.g., potatoes, grains, cereals, etc. In this case, the method allows for protection of the plant matter and extension of their preservation.

According to a first embodiment, the gas flow containing the essential oil vapour is injected continuously into the site. The amount of essential oil injected daily is calculated based on the requirements of the treatment to be carried out. This amount is based typically on the type of plant matter to treat, the amount of plant matter stored in the site, and the type of essential oil contained in the gas flow.

In one variant, the gas flow containing the essential oil vapour is injected intermittently into the site. This would be the case, e.g., when the amount of essential oil to be provided is low compared to the production capacity of the device producing the gas flow. In the case of continuous injection, this would result in choosing a very low essential oil vapour concentration, very far from the saturation pressure (e.g., 10% of the saturation pressure). In this case, it is more advantageous only to inject the gas flow a few hours a day, with no injections occurring the rest of the time. This allows for energy to be saved and wear on the gas flow production device containing the essential oil vapour to be reduced.

For example, the gas flow is injected into the site every day for between one minute every hour and ten minutes every hour, or for a duration of 0.5-24 h per day, preferably 0.5-5 h, and more preferably 2-3 h per day.

Typically, the start and stop of the injection are automatic, and managed by a computer. Alternatively, the start and stop of the injection are carried out manually.

According to another embodiment, the gas flow is created within the site, with the liquid composition injected into the gas flow within the site.

If the site has a given internal volume and a given temperature, the mass of the essential oil injected each day is preferably chosen such that the mass, dispersed uniformly in the internal volume and entirely present as vapour, leads to a partial pressure of the essential oil vapour at least 20% less than the partial saturation pressure of the essential oil vapour at that given temperature. Thus, each day, an amount of essential oil is injected that cannot cause the formation of droplets, assuming that this amount is entirely in the form of vapour and is homogeneously dispersed throughout the internal volume.

According to a third aspect, the invention concerns a device suited to produce a gas flow containing an essential oil vapour according to the aforementioned method of production, comprising:

- an organ for producing a pressurised gas flow production with a given temperature;
- a reservoir containing a liquid composition comprising at least one liquid essential oil;
- an organ for injecting a liquid composition into the pressurised gas flow from the reservoir at a dosed flow rate; and
- an assembly for controlling the flow rate of the gas flow and the flow rate of the liquid composition, adapted so that the gas flow, following injection, has a partial essential oil vapour pressure at least 20% below the saturation pressure of the essential oil vapour at the temperature of the gas flow.

Advantageously, the control assembly includes a computer to program the frequency and duration of injection of the liquid composition.

According to a first embodiment, this device is similar to a thermal fogging device, but different. Thermal fogging devices are described, e.g., in FR 2938458, FR 2791910, or FR 2566681. Thermal fogging seeks to generate a mist of very fine aerosol droplets. For example, at least 90% of the droplets has a diameter of less than 3 μm. Typically, in such a method, an aqueous solution is injected into a very hot gas (e.g., 550-750° C.) circulating at high speed (160-400 m/s). Such a device is not suited for the production of a gas flow containing an essential oil vapour, as the temperature and flow rate ranges of the injection of the liquid composition into the gas are not suitable.

According to this first embodiment, the device comprises an organ for heating the pressurised gas flow.

Additionally, the control assembly, in this embodiment, is suited for controlling the flow rate of the gas flow after injection such that the gas flow, following injection, has a partial essential oil vapour pressure at least 20% below the saturation pressure of the essential oil vapour at the temperature of the gas flow.

According to a second embodiment, the device comprises a porous element arranged upstream of the pressurised gas flow production organ and suited to receive the liquid composition.

In one variant, the porous element is arranged downstream of the pressurised gas flow production organ.

Typically, the porous element is formed by a rubbery material such as an open-cell latex plate.

The porous element allows for recovery of the liquid composition that was not injected into the gas flow by aspiration of the gas flow production organ, thus preventing drops of liquid composition from falling, e.g., on the plant matter to be treated.

Typically, in this second embodiment, the gas flow production organ consists of one or more fans provided to circulate the air within the area.

According to a fourth aspect, the invention concerns an assembly for treating a site, comprising:

- a site; and
- a device for producing a gas flow containing an essential oil vapour as described above.

According to a first embodiment, the gas flow production device is arranged to inject the gas flow into the site.

According to a second embodiment, the gas flow production device is arranged to create the gas flow within the site.

The site is, e.g., a room in a hospital or school, a factory or any other building for medical, administrative, educational, or industrial use. The site may also be a confined area intended for the storage of plant matter. The confined area is empty, or contains plant matter, as described above.

The production device is typically installed outside of the site. In one variant, it is installed inside the site.

BRIEF DESCRIPTION OF THE DRAWING FIGURES

Other characteristics and benefits of the invention can be seen from the detailed description provided below, by way of example only, in reference to the attached drawings, of which:

FIG. 1 is a simplified schematic representation of a device for producing a gas flow containing an essential oil vapour according to the invention; and FIG. 2 is a simplified schematic representation of a first embodiment of an assembly for treating a confined area, comprising the device of FIG. 1;

FIG. 3 is a simplified schematic representation of a second embodiment of an assembly for treating a confined area.

DETAILED DESCRIPTION OF THE INVENTION

The device 1 shown in FIG. 1 is intended to produce a gas flow containing an essential oil vapour. The essential oil is entirely in the form of vapour in the gas flow, which does not contain any droplets of essential oil.

Such a device is typically provided for the sterilisation of sites or the treatment of food products such as fruits and vegetables stored in closed areas, in particular greenhouses or storerooms, or the treatment of silos that are empty or filled with grain.

The device 1 comprises:

- an assembly 3 for producing a hot pressurised gas flow;
- an ejection opening 5;
- a reservoir 7 containing a liquid composition comprising at least one liquid essential oil;
- an organ 9 for injecting a liquid composition into the hot pressurised gas flow from the reservoir 7 at a dosed flow rate; and
- a computer 11 controlling the assembly 3 and the injection organ 9.

The production assembly 3 includes a blower 13 and a heating organ 15. The blower 13 has an inlet 17 for aspirating atmospheric air and an outlet 19 for pressurised air.

The heating organ 15 includes a casing 21, a heating electrical resistance 23, and an electrical power supply 25 electrically connected to the heating resistance 23. The heating resistance 23 is located inside the casing 21. The casing 21 has a cold gas inlet connected to the outlet 19 of the blower, and a convergent section 27 delimiting an outlet 29 for hot pressurised gas.

The ejection tube 5 is a straight, cylindrical tube. It is open on both ends. One of the ends delimits an inlet for hot gas, is connected to the outlet 29 of the heating organ. The opposite end delimits an ejection opening of the hot gad containing the essential oil vapour. This outlet is designated by reference number 31. Additionally, the ejection tube has an input 33 for liquid located near the hot gas inlet.

The injection organ 9 is a dosing pump. A suction tube 37 connects the suction inlet of the pump 9 with the reservoir 7. A discharge duct 39 connects a discharge outlet of the dosing pump 9 to the liquid input 33 of the ejection tube.

A temperature probe 41 is placed in the ejection tube 5, upstream of the liquid inlet 33. It is preferably placed near the inlet 33. It provides information to the computer 11.

The computer 11 is connected to the dosing pump 9, the electrical generator 25, and the blower motor 13. The computer 11 is suited to control each of these elements.

The blower 17, between blowing and suction, has a pressure difference between $0.20 \times 10^5$ Pa and $0.30 \times 10^5$ Pa. The flow rate of the blower can be set between 10 and 200 Nm$^3$/h. The electrical resistance 23 is sized so as to be able to heat the air flow from the blower to a temperature between 70 and 250° C. at the inlet of the tube 5. The electrical power of the resistance can be set, e.g., between 0 and 12 kW. The dosing pump 9 has a flow rate that can be set, e.g., between 0.1 and 10 l/h.

The operation of the production device 1 above will be described below.

The user first enters into the computer lithe setpoints for the flow rate of the air exiting the blower 13, for the temperature for the air flow exiting the heater 15, and the flow rate of the liquid composition to be injected by the dosing pump 9.

The computer 11 then sends the start command to the blower 13 and the electrical power of the resistance 23. The blower 13 aspirates atmospheric air and blows it out through the heater 15 to the tube 5. The dosing pump 9 is stopped.

When the temperature measured by the probe 41 reaches the setpoint, the computer 11 sends the start command to the dosing pump 9. The liquid composition is aspirated by the dosing pump 9 in the reservoir 7, and is sent by the pump to the inlet 33. This liquid composition is then injected into the hot gas flow from the heater. The liquid composition is dispersed in the hot gas flow and evaporates. The gas flow loaded with essential oil vapour exits the ejection tube 5 via the outlet 31.

The setpoints for the flow rate of the gas flow, the temperature of the gas flow, and the flow rate of the liquid composition are chosen by the user such that the gas flow, following injection, has a partial essential oil vapour pressure of at least 20% below the saturation pressure of the essential oil vapour at the temperature setpoint.

The computer 11 continuously controls the gas flow rate, the gas flow temperature, and the flow rate of the liquid composition in order to keep them at their setpoints.

FIG. 2 shows a first embodiment of an assembly for treating a confined area, comprising the device of FIG. 1.

According to FIG. 2, the production device 1 of FIG. 1 is typically integrated into an assembly 43 for treating an area 45. The assembly 43 comprises:

the confined area 45:

the device 1 for producing a gas flow containing an essential oil vapour, arranged so as to inject the gas flow into the confined area 45.

The area 45, in the example, is represented by a room delimiting an internal volume 47, in which plant matter 49 is stored. The plant matter 49 only occupies part of the internal volume 47. The area 45 is equipped with one or more fans 51, arranged in the internal volume 47, provided to circulate the air within the area 45. The device 1 is placed outside of the area 45. The tube 5 traverses the area 45, such that the outlet 31 opens into the internal volume.

The computer 11 is programmed to operate the device 1 at a predetermined interval, and with a predetermined setpoint. The frequency typically corresponds to operation a few hours every day. The duty point is defined by the setpoints for the gas flow rate, the gas flow temperature, and the flow rate of the liquid composition, determined depending on the type of plant matter to be treated, the quantity stored in the area, and the type of essential oil applied. The frequency is chosen depending on the amount of essential oil to be applied.

In one exemplary embodiment, the area has an internal volume of 4000 m3, and stores 1000 tonnes of potatoes. The essential oil applied is mint oil. 90 g mint oil is applied each month and per tonne of potatoes. The temperature in the area is 7° C.

The production device 1 operates 3 minutes per hour. The flow rate of the air generated by the blower is 50 $Nm^3/h$. The heat output of the resistance 23 is approximately 4.7 kW. The temperature setpoint is 220° C. The liquid composition is a mixture of ⅔ clove oil and ⅓ mint oil. The injection flow rate setpoint of the dosing pump 9 is 4 l/h, corresponding to one injection of approximately 3 kg per day of mint oil. In the internal volume, an average partial pressure of mint oil below the saturation pressure is obtained. In fact, a total of 3 kg mint oil per day is injected. By comparison, at saturation pressure, at 7° C., a volume of 4000 $m^3$ contains 4 mint oil. Any risk of condensation in the internal volume is thus eliminated. The 3 kg mint oil is absorbed by the potatoes in one day.

FIG. 3 shows a second embodiment of an assembly for treating a confined area.

According to this figure, the assembly 43 for treating an area 45 comprises:

the confined area 45 delimiting the internal volume 47;

the device 1 for producing a gas flow containing an essential oil vapour, arranged so as to create the gas in the confined area 45.

In this example, the device 1 comprises the liquid essential oil composition reservoir 7, the liquid composition dosing pump 9, an injection tube for injecting the liquid composition into the area 45, and one or more fans 51 arranged in the area 45. It further comprises an open-cell latex plate 53 arranged upstream of the fan(s) 51. It also comprises a computer 11 suited to control the gas flow rate and the flow rate of the liquid composition.

In this example, like the embodiment described in FIG. 2, the fan 51 circulates the air in the area 45. The fan 51 has an elevated flow rate. The gas flow is thus created in the area by means of a fan 51.

The liquid composition is injected into the area 45 at a low flow rate, e.g., 0.1 l/h, such that the drops of the liquid composition are carried by the gas flow aspirated into the fan 51. Thus, the injection of the liquid composition upstream of the fan 51 allows for the evaporation of the liquid composition without any need for preheating.

In this example, the assembly 43, at a gas flow temperature of 5° C., allows for the evaporation of 2 g essential oil per cubic meter of air.

The drops of liquid composition that are not injected into the gas flow aspirated into the fan 51 are deposited on the open-cell latex plate 53 arranged upstream of the suction of the fan 51. Thus, the latex plate absorbs the drops of liquid composition and prevents them spilling onto the plant matter to be treated.

Thus, this embodiment allows for the cold evaporation of the liquid composition injected into the area 45.

In one variant of this second embodiment, an atomiser is placed at the suction of the fan 51, at the outlet of the injection tube for the liquid composition in the area 45. The atomiser thus vaporises the liquid composition at the suction of the fan 51. The atomiser allows for the formation of fine droplets of essential oil at the suction of the fan 51, thus facilitating the evaporation of the composition injected.

Thus, it can be seen that the method and device for production of a gas flow according to the invention allow for the production of elevated concentrations of essential oil, possibly slightly below the saturation of the essential oil in the atmosphere, for long periods of time and large volumes.

The risk of condensation of the essential oil on the products stored, and thus the phytotoxicity of the essential oil, is thus avoided.

The invention claimed is:

1. A method for producing a gas flow containing an essential oil vapour or a vapour of one or more terpenoid compounds contained in the essential oil, comprising the following steps:
   creation of a pressurised gas flow with a controlled flow-rate and a given temperature; and
   injection into the pressurised gas flow of a liquid composition comprising at least one liquid essential oil, at a dosed flow rate;
   the gas flow, following injection, having a partial essential oil vapour pressure,
   whereby the flow rate of the gas flow and the flow rate of the liquid composition are chosen such that the partial essential oil vapour pressure of the gas flow, following injection, is controlled to be at least 20% below the saturation pressure of the essential oil vapour at the temperature of the gas flow.

2. The method according to claim 1, wherein the flow rate of the gas is controlled between 10 and 200 Nm$^3$/h.

3. The method according to claim 1, wherein the flow rate of the liquid composition is controlled so that the mass of the essential oil injected into the gas flow is between 0.1 and 50 kg/h.

4. The method according to claim 1, characterised in that the pressurised gas flow is created by a organ for producing the pressurised gas flow.

5. The method according to claim 1, further comprising a step of depositing the liquid composition in a porous element arranged upstream or downstream of the production organ of the pressurised gas flow.

6. The method according to claim 5, wherein the porous element is and open-cell latex plate.

7. The method according to claim 1, wherein the liquid composition is injected using a dosing pump.

8. The method according to claim 1, wherein the pressurised gas flow has a controlled temperature, whereby the temperature is controlled such that the gas flow, following injection, has a partial essential oil vapour pressure at least 20% below the saturation pressure of the essential oil vapour at the controlled temperature.

9. The method according to claim 8, wherein the gas flow temperature is controlled between 50 and 350° C.

10. The method according claim 1, wherein the liquid composition comprises at least one essential oil selected from the group consisting of mint oil, clove oil, rose oil, thyme oil, oregano oil, or at least one of their constituents from the group of L-carvone, eugenol, geraniol, thymol, carvacrol, pyrethrum and volatile synthetic molecules with biocidal properties.

11. The method according to claim 1, wherein the partial pressure of the essential oil vapour is controlled by adjusting the amount of liquid composition injected compared to the amount of gas.

12. The method according to claim 1, wherein partial pressure of the essential oil vapour is controlled by modifying the amount of liquid composition injected and/or the flow-rate of the gas flow.

13. The method according to claim 1, wherein a computer controls the flow-rate of the gas flow, the temperature of the gas and the flow rate of the liquid composition.

14. The method according to claim 13, wherein a user enters in the computer setpoints for the flow-rate of the gas flow, for the temperature of the gas and for the flow rate of the liquid composition, such that the partial essential oil vapour pressure is at least 20% below the saturation pressure of the essential oil vapour at the temperature setpoint.

15. The method according to claim 14, wherein after the user has entered the setpoints, the computer sends a start command to means for creating the gas flow with a controlled flow rate and an electric power to means for heating the gas flow, no liquid composition being injected into the gas flow, and when the temperature of the gas flow reaches the setpoint, the computer sends the start command to the means for injection the liquid composition into the gas flow.

16. The method according to claim 14, wherein the computer continuously controls the flow-rate of the gas flow, the temperature of the gas flow and the flow rate of the liquid composition in order to keep them at their setpoints.

\* \* \* \* \*